US010584191B2

(12) United States Patent
Bakar et al.

(10) Patent No.: US 10,584,191 B2
(45) Date of Patent: Mar. 10, 2020

(54) ANTIMICROBIAL STAR POLYMERS WITH LIGHT-ACTIVATED ENHANCED ANTIMICROBIAL ACTIVITY (71) Applicant: International Business Machines Corporation, Armonk, NY (US)

(72) Inventors: Mohd Bakri Bakar, Skudai (MY); James L. Hedrick, Pleasanton, CA (US); Victoria A. Piunova, Los Gatos, CA (US); Andy Theodora Tek, San Jose, CA (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 15/824,153

(22) Filed: Nov. 28, 2017

(65) Prior Publication Data

US 2019/0161562 A1   May 30, 2019

(51) Int. Cl.
C08F 8/42 (2006.01)
A01N 55/02 (2006.01)
C09D 5/14 (2006.01)
C09D 153/00 (2006.01)
A01N 25/00 (2006.01)
A01N 25/10 (2006.01)

(52) U.S. Cl.
CPC ............... *C08F 8/42* (2013.01); *A01N 25/00* (2013.01); *A01N 25/10* (2013.01); *A01N 55/02* (2013.01); *C09D 5/14* (2013.01); *C09D 153/005* (2013.01)

(58) Field of Classification Search
CPC ......... C08F 8/42; C09D 153/005; C09D 5/14; A01N 55/02; A01N 25/00; A01N 25/10
See application file for complete search history.

(56) References Cited

U.S. PATENT DOCUMENTS

| 8,765,098 B2 | 7/2014 | Appel et al. |
| 8,945,513 B2 * | 2/2015 | Lee ............... A61K 49/0036 424/9.322 |
| 2012/0251608 A1 | 10/2012 | Coady et al. |
| 2014/0370064 A1 | 12/2014 | Lee et al. |

(Continued)

FOREIGN PATENT DOCUMENTS

| CN | 103501769 | 1/2014 |
| CN | 104861172 A | 8/2015 |

OTHER PUBLICATIONS

List of IBM Patents or Applications Treated as Related, Jan. 4, 2018.

(Continued)

*Primary Examiner* — Jianfeng Song
(74) *Attorney, Agent, or Firm* — Amin, Turocy & Watson, LLP (57) ABSTRACT Techniques regarding a star polymer with light-activated enhanced antimicrobial functionality are provided. For example, a polymer is provided that can comprise a plurality of non-degradable copolymer arms comprising respective first ends and respective second ends. The respective first ends can be crosslinked to form a vinyl polymer core and the respective second ends can have antimicrobial functionality. Further, the polymer can comprise a singlet oxygen generator loaded within the vinyl polymer core. The singlet oxygen generator can generate a singlet oxygen species in response to light.

4 Claims, 10 Drawing Sheets (56) References Cited

U.S. PATENT DOCUMENTS

2015/0335760 A1 11/2015 Lee et al.
2016/0338356 A1 11/2016 Chin et al.

OTHER PUBLICATIONS

International Search report for PCT/IB2018/058797 dated Feb. 11, 2019, 9 pages.
Non-Final Office Action received for U.S. Appl. No. 15/824,250 dated May 20, 2019, 137 pages.
Bing, Synthesis of Novel Photoactive Degradable Polymers with Potential in Biomedical Applications, The Hong Kong Polytechnic University, 2014.
Zhao, et al., Cationic Oligo(thiophene ethynylene) with Broad-Spectrum and High Antibacterial Efficiency under White Light and Specific Biocidal Activity against *S. aureus* in Dark, ACS Appl. Mater. Interfaces 2016, pp. 1019-1024, vol. 8.
Xing, et al., Conjugated Polymer/Porphyrin Complexes for Efficient Energy Transfer and Improving Light-Activated Antibacterial Activity, J. Am. Chem. Soc., Aug. 24, 2009, pp. 13117-13124.
Hynek, et al., Design of porphyrin-based conjugated microporous polymers with enhanced singlet oxygen productivity, RSC Adv., 2016, pp. 44279-44287, vol. 6.
Vatansever, et al., Antimicrobial strategies centered around reactive oxygen species—bactericidal antibiotics, photodynamic therapy and beyond, FEMS Microbiol. Rev., May 16, 2013, pp. 955-989, vol. 37.
Oyinloye, et al., Reactive Oxygen Species, Apoptosis, Antimicrobial Peptides and Human Inflammatory Diseases, Pharmaceuticals 2015, pp. 151-175, vol. 8.
Kammerlander, et al., A clinical evaluation of the efficacy and safety of singlet oxygen in cleansing and disinfecting stagnating wounds, Journal of Wond Care, Apr. 2011, pp. 149-150, vol. 20, No. 4.
Stoller, et al., Oxygen Therapy for Patients With COPD Current Evidence and the Long-Term Oxygen Treatment Trial, CHEST Recent Advances in Chest Medicine, Jul. 2010, pp. 179-187, vol. 138(1).
Fuhrhop, et al., Porphyrin Assemblies and Their Scaffolds, Langmuir, 2014, pp. 1-12, vol. 30(1).
Lee, et al., Nanogel Star Polymer Architectures: A Nanoparticle Platform for Modular Programmable Macromolecular Self-Assembly, Intercellular Transport, and Dual-Mode Cargo Delivery, Advanced Materials, 2011, pp. 4509-4515, vol. 23.
Appel, et al., Toward biodegradable nanogel star polymers via organocatalytic ROP, Chem. Commun, 2012, pp. 6163-6165, vol. 48.
Yang, et al., Broad-Spectrum Antimicrobial Star Polycarbonates Functionalized with Mannose for Targeting Bacteria Residing inside Immune Cells, Advanced Healthcare Materials, Mar. 2016, pp. 1-11.
Kralova, et al., Glycol Porphyrin Derivatives as Potent Photodynamic Inducers of Apoptosis in Tumor Cells, Journal of Medicinal chemistry, 2008, pp. 5964-5973, vol. 51.
Chan, et al., Tetra-n-butylammonium Fluoride as an Efficient Transesterification Catalyst for Functionalizing Cyclic Carbonates and Aliphatic Polycarbonates, ACS Macro Letteres, 2013, pp. 860-864, vol. 2.
Dove, et al. Thiourea-Based Bifunctional Organocatalysis: Supramolecular Recognition for Living Polymerization, J. Am. Chem. Soc., 2005, pp. 13798-13799, vol. 127.
Lohmeijer, et al., Guanidine and Amidine Organocatalysts for Ring-Opening Polymerization of Cyclic Esters, Macromolecules, 2006, pp. 8574-8583.
Chin, et al., Biodegradable Broad-Spectrum Antimicrobial Polycarbonates: Investigating the Role of Chemical Structure on Activity and Selectivity, Macromolecules, 2013, pp. 8797-8807, vol. 46.
Rumyantseva, et al., Improved Method of 5,10,15,20-Tetrakis(4-hydroxyphenyl)-porphyrins Synthesis, Macroheterocycles, 2013, pp. 59-61, vol. 6(1).
List of IBM Patents or Applications Treated as Related.

* cited by examiner

902 — DISPOSING ON A SURFACE OF AN ARTICLE A FILM-FORMING COMPOSITION, THE FILM-FORMING COMPOSITION COMPRISING: A SOLVENT; AND A STAR POLYMER COMPRISING GREATER THAN OR EQUAL TO 5 WEIGHT PERCENT OF THE FILM-FORMING COMPOSITION AND LESS THAN OR EQUAL TO 20 WEIGHT PERCENT OF THE FILM-FORMING COMPOSITION, WHEREIN THE STAR POLYMER IS DISPERSED IN THE SOLVENT AND THE STAR POLYMER COMPRISES: A PLURALITY OF NON-DEGRADABLE COPOLYMER ARMS COMPRISING RESPECTIVE FIRST ENDS AND RESPECTIVE SECOND ENDS, WHEREIN THE RESPECTIVE FIRST ENDS ARE CROSSLINKED TO FORM A VINYL POLYMER CORE AND THE RESPECTIVE SECOND ENDS HAVE ANTIMICROBIAL FUNCTIONALITY; AND A SINGLET OXYGEN GENERATOR LOADED WITHIN THE VINYL POLYMER CORE, WHEREIN THE SINGLET OXYGEN GENERATOR GENERATES A SINGLET OXYGEN SPECIES IN RESPONSE TO LIGHT

904 — REMOVING THE SOLVENT FROM THE SURFACE OF THE ARTICLE

906 — APPLYING A TREATMENT TO THE FILM-FORMING COMPOSITION SELECTED FROM A GROUP CONSISTING OF A THERMAL TREATMENT AND A PHOTOCHEMICAL TREATMENT

FIG. 10

CONTACTING A PATHOGEN WITH A POLYMER, THE POLYMER COMPRISING: A PLURALITY OF NON-DEGRADABLE COPOLYMER ARMS COMPRISING RESPECTIVE FIRST ENDS AND RESPECTIVE SECOND ENDS, WHEREIN THE RESPECTIVE FIRST ENDS ARE CROSSLINKED TO FORM A VINYL POLYMER CORE AND THE RESPECTIVE SECOND ENDS HAVE ANTIMICROBIAL FUNCTIONALITY; AND A SINGLET OXYGEN GENERATOR LOADED WITHIN THE VINYL POLYMER CORE, WHEREIN THE SINGLET OXYGEN GENERATOR GENERATES A SINGLET OXYGEN SPECIES IN RESPONSE TO LIGHT, WHEREIN UPON CONTACT WITH THE PATHOGEN, THE POLYMER ELECTROSTATICALLY DISRUPTS A MEMBRANE OF THE PATHOGEN  1002

IRRADIATING THE STAR POLYMER WITH LIGHT, AND GENERATING THE SINGLET OXYGEN SPECIES VIA THE SINGLET OXYGEN GENERATOR LOADED WITHIN THE VINYL POLYMER CORE  1004

ANTIMICROBIAL STAR POLYMERS WITH LIGHT-ACTIVATED ENHANCED ANTIMICROBIAL ACTIVITY

BACKGROUND

The subject disclosure relates to a star polymer with antimicrobial activity, and more specifically, to a star polymer loaded with an oxygen singlet generator to provide light-activated enhanced antimicrobial activity.

SUMMARY

The following presents a summary to provide a basic understanding of one or more embodiments of the invention. This summary is not intended to identify key or critical elements, or delineate any scope of the particular embodiments or any scope of the claims. Its sole purpose is to present concepts in a simplified form as a prelude to the more detailed description that is presented later. In one or more embodiments described herein, compositions and methods regarding star polymers loaded with one or more oxygen singlet generators to provide light-activated enhanced antimicrobial activity are described.

According to an embodiment, a polymer is provided. The polymer can comprise a plurality of non-degradable copolymer arms that can comprise respective first ends and respective second ends. The respective first ends can be crosslinked to form a vinyl polymer core and the respective second ends can have antimicrobial functionality. The polymer can further comprise a singlet oxygen generator loaded within the vinyl polymer core, wherein the singlet oxygen generator can generate a singlet oxygen species in response to light.

According to an embodiment, a method is provided. The method can comprise mixing a star polymer with a singlet oxygen generator in anhydrous solvent to form a solution. The singlet oxygen generator can generate a singlet oxygen species in response to light. The star polymer can comprise a plurality of non-degradable copolymer arms that can have respective first ends and respective second ends, wherein the respective first ends can be crosslinked to form a vinyl polymer core and the respective second ends can have antimicrobial functionality. The method can further comprise sparging the solution with nitrogen gas for a defined period of time.

According to an embodiment, a film-forming composition is provided. The film forming composition can comprise a solvent and a star polymer. The star polymer can comprise greater than or equal to 5 weight percent of the film-forming composition and less than or equal to 20 weight percent of the film-forming composition. Also, the star polymer can be dispersed within the solvent. Further, the star polymer can comprise a plurality of non-degradable copolymer arms that can comprise respective first ends and respective second ends, wherein the respective first ends can be crosslinked to form a vinyl polymer core and the respective second ends can have antimicrobial functionality. Moreover, the star polymer can comprise a singlet oxygen generator loaded within the vinyl polymer core, wherein the singlet oxygen generator can generate a singlet oxygen species in response to light.

According to an embodiment, a method of forming a surface treated article is provided. The method can comprise disposing on a surface of an article a film-forming composition. The film-forming composition can comprise a solvent and a star polymer. The star polymer can comprise greater than or equal to 5 weight percent of the film-forming composition and less than or equal to 20 weight percent of the film-forming composition. Also, the star polymer can be dispersed in the solvent. Additionally, the star polymer can comprise a plurality of non-degradable copolymer arms that can comprise respective first ends and respective second ends, wherein the respective first ends can be crosslinked to form a vinyl polymer core and the respective second ends can have antimicrobial functionality. The star polymer can also comprise a singlet oxygen generator loaded within the vinyl polymer core, wherein the singlet oxygen generator can generate a singlet oxygen species in response to light. The method can further comprise removing the solvent from the surface of the article.

According to an embodiment, a method of killing a pathogen is provided. The method can comprise contacting the pathogen with a polymer. The polymer can comprise a plurality of non-degradable copolymer arms that can comprise respective first ends and respective second ends, wherein the respective first ends can be crosslinked to form a vinyl polymer core and the respective second ends can have antimicrobial functionality. The polymer can also comprise a singlet oxygen generator loaded within the vinyl polymer core, wherein the singlet oxygen generator can generate a singlet oxygen species in response to light. Upon contact with the pathogen, the polymer can electrostatically disrupt a membrane of the pathogen.

DETAILED DESCRIPTION

The following detailed description is merely illustrative and is not intended to limit embodiments and/or application or uses of embodiments. Furthermore, there is no intention to be bound by any expressed or implied information presented in the preceding Background or Summary sections, or in the Detailed Description section.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

In the recent decades, there has been a rise in antibiotic-resistant bacteria. Systemic overuse of broad-spectrum antibiotics has lead to a rise in multi-drug resistant bacteria commonly referred to as "superbugs." Further, biofilms can form on human tissue and implanted devices, leading to implant failure. The biofilms can be composed of bacteria embedded within a self-produced extracellular polymeric matrix. Thus, the biofilms can be difficult to penetrate, thereby rendering it difficult to kill the embedded bacteria.

As an alternative to conventional antibiotic techniques, reactive oxygen species (ROS) can exhibit strong antimicrobial, antiviral, and antifungal activity. Multiple reports claim that ROS can have high efficacy against various pathogens such as, but not limited to: Gram-positive bacteria, Gram-negative bacteria, fungi, and yeast. Further, ROS can be effective in cleansing and/or treating stagnate wounds and treating chronic obstructive pulmonary disease. Unfortunately, while ROS can be toxic to various pathogens, they can be equally as toxic against host cells. Additionally, conventional ROS can be unstable and exhibit undesirable burst releases.

Various embodiments described herein can provide compositions (e.g., film-forming compositions) and/or methods for the synthesis and/or use of antimicrobial star polymers with enhanced activity provided by reactive oxygen generating functionalities. As used herein, the term "star polymer" can refer to a polymer having a plurality of arms crosslinked together to form a central core. For example, one or more embodiments can comprise a nanogel star polymer that can have a plurality of positively charged non-degradable block polymer arms crosslinked to form a hydrophobic vinyl polymer core loaded with a singlet oxygen generator. In various embodiments, a film-forming composition can comprise the polymer compositions described herein. Further, one or embodiments can regard methods utilizing the polymer composition and/or film-forming composition to kill, and/or prevent contamination and/or growth of, various pathogens (e.g., Gram-positive bacteria, Gram-negative bacteria, fungi, and yeast) and/or surface treat various articles (e.g., food and/or medical packaging).

Figure 1:
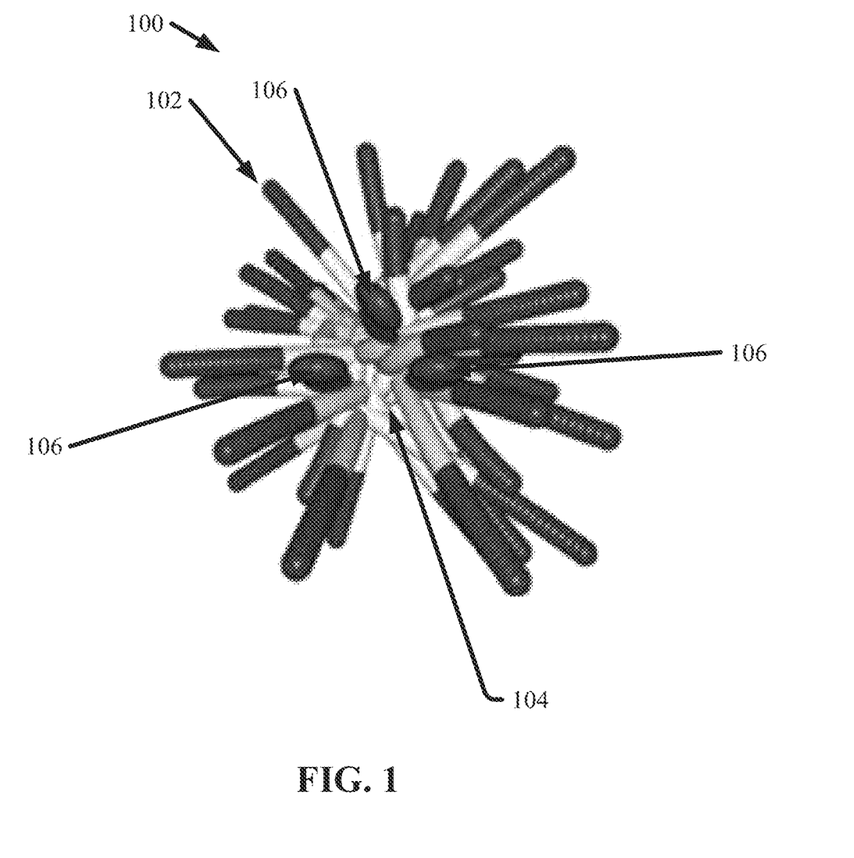
FIG. 1 illustrates a three-dimensional drawing of an example, non-limiting star polymer loaded with one or more singlet oxygen generators in accordance with one or more embodiments described herein.

FIG. 1 illustrates a three-dimensional drawing of an example, non-limiting loaded star polymer 100. The loaded star polymer 100 can comprise a plurality of arms 102 crosslinked to form a polymer core 104. Additionally, the loaded star polymer can comprise one or more singlet oxygen generators 106 loaded within, and/or adjacent to, the polymer core 104. In various embodiments, the loaded star polymer 100 can crosslink with one or more additional star polymers (e.g., loaded star polymer 100) without the assistance of an additional chemical crosslinking agent and/or photochemical activation. The crosslinking can be chemical (e.g., covalent bonds), physical (e.g., hydrophobic bonding, chain entanglement, and/or ionic association), and/or a combination thereof. The plurality of arms 102 can be present in the loaded star polymer 100 as homopolymers, random copolymers, block polymers, and/or a combination thereof. Additionally, in various embodiments, the plurality of arms 102 can be non-degradable.

In various embodiments, the loaded star polymer 100 can comprise one or more functionalization sites that can be utilized to control chemical interactions that can facilitate antimicrobial and/or film-forming properties. For example, one or more of the arms 102 and/or the polymer core 104 can be capable of further chain growth.

Figure 2:
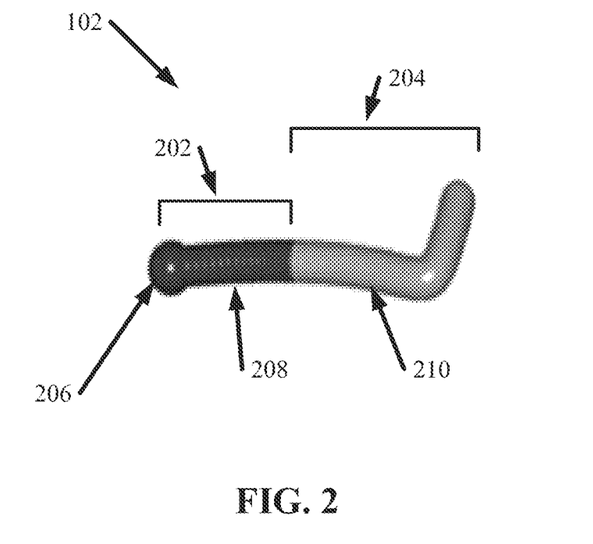
FIG. 2 illustrates a drawing of an example, non-limiting arm that can comprise a loaded star polymer in accordance with one or more embodiments described herein.

FIG. 2 illustrates a drawing of an example, non-limiting arm 102 that can comprise the loaded star polymer 100. Repetitive description of like elements employed in other embodiments described herein is omitted for sake of brevity. In various embodiments, the arm 102 can be a non-degradable block copolymer comprising a first block 202 and a second block 204. Further, the arm 102 can comprise cationic, anionic, and/or non-cationic groups. The loaded star polymer 100 can comprise greater than or equal to six arms 102 and less than or equal to one hundred arms 102. For example, in various embodiments, the loaded star polymer 100 can comprise greater than or equal to fifteen arms 102 and less than or equal to fifty arms 102. Additionally, the plurality of arms 102 can exhibit antimicrobial functionality.

In one or more embodiments, the first block 202 can comprise a reactive end group 206 and/or a first unit 208. Further, in various embodiments the first block 202 can be hydrophilic. The reactive end group 206 can facilitate self-crosslinking of the loaded star polymer 100 with another star polymer (e.g., another loaded star polymer 100). The reactive end group 206 can comprise a halide ion located alpha to a carbonyl group and/or alpha to an aromatic ring. Example, halide ions include: fluoride, chloride, bromide, iodide, and astatide. Example carbonyl groups include, but are not limited to: alpha-halo ketones, alpha-halo esters, alpha-halo acids, alpha-halo amides, and/or a combination thereof. Example aromatic rings include, but are not limited to: phenyl, pyridinyl, and/or the like.

In various embodiments, the reactive end group 206 can be a product of polymerization used to form the arm 102. For example, the reactive end group 206 can comprise: an epoxide (e.g., from anionic polymerization), an alkoxyamine (e.g., from controlled radical polymerization), a dithioester (e.g., from reversible addition-fragmentation transfer polymerization), and/or a trithiocarbonate (e.g., from reversible addition-fragmentation transfer polymerization). In one or more embodiments, the reactive end group 206 can be prepared by chemically modifying the peripheral end of the arm 102. For example, the peripheral end of the arm 102 can be modified to produce a reactive end group 206 including, but not limited to: an azide, a thiol, an olefin, and/or an aryl substituted ketone.

In one or more embodiments, the reactive end group 206 can be covalently boded to the first unit 208. The first unit 208 can comprise primary amines, secondary amines, tertiary amines, quaternary amines, tertiary phosphines, quaternary phosphines, cationic protonated forms of the forgoing, a combination thereof, and/or the like. Also, in various embodiments the first unit 208 can repeat 'm' number of times, wherein 'm' can be an integer greater than or equal to 2 and less than or equal to 100. In some embodiments 'm' can be an integer greater than or equal to 2 and less than or equal to 10000. For example, the first unit 208 can repeat fifty times. Example first units 208 can include, but are not limited to: substituted (meth)acrylates and acrylamides. In other embodiments, any other compounds that have antimicrobial functionality (e.g., a positively charged moieties can comprise the first unit 208.

The first block 202 can be covalently boded to the second block 204. The second block 204 can be hydrophobic. The second block can comprise one or more second units 210. The second unit 210 can comprise a vinyl polymer structure. Example, vinyl polymer structures include, but are not limited to: styrene, substituted styrene, divinylbenzene, substituted divinylbenzene, a (meth)acrylate ester, an ethylene glycol di(meth)acrylate, a (meth)acrylamide, an acrylonitrile, vinyl acetate, vinyl chloride, ethene, propene, butadiene, a combination thereof, and/or the like. The second block 204 of one respective arm 102 can crosslink (e.g., chemically and/or physically) with another second block 204 of another respective arm 102. Thus, a plurality of second blocks 204 can crosslink to form the polymer core 104 of the loaded star polymer 100. For example, wherein the second unit 210 comprises a vinyl polymer structure, a plurality of second blocks 204 (e.g., comprising a plurality of arms 102) can have a crosslinked structure to form a vinyl polymer core 104. Also, in various embodiments the second unit 210 can repeat 'n' number of times, wherein 'n' can be an integer greater than or equal to 2 and less than or equal to 100. In some embodiments, 'n' can be an integer greater than or equal to 2 and less than or equal to 10000. For example, the second unit 210 can repeat thirty times. In other embodiments, any other vinyl polymer compound with an affinity for crosslinking can comprise the second unit 210.

Thus, in various embodiments, the arm 102 can be a non-degradable copolymer and can comprise: a first end (e.g., first block 202) having antimicrobial functionality, and a second end (e.g., second block 204) that can crosslink with another arm 102 to form a polymer core 104. Further, the first ends can be positively charged (e.g., via the first unit 208) to facilitate antimicrobial functionality.

Figure 3:
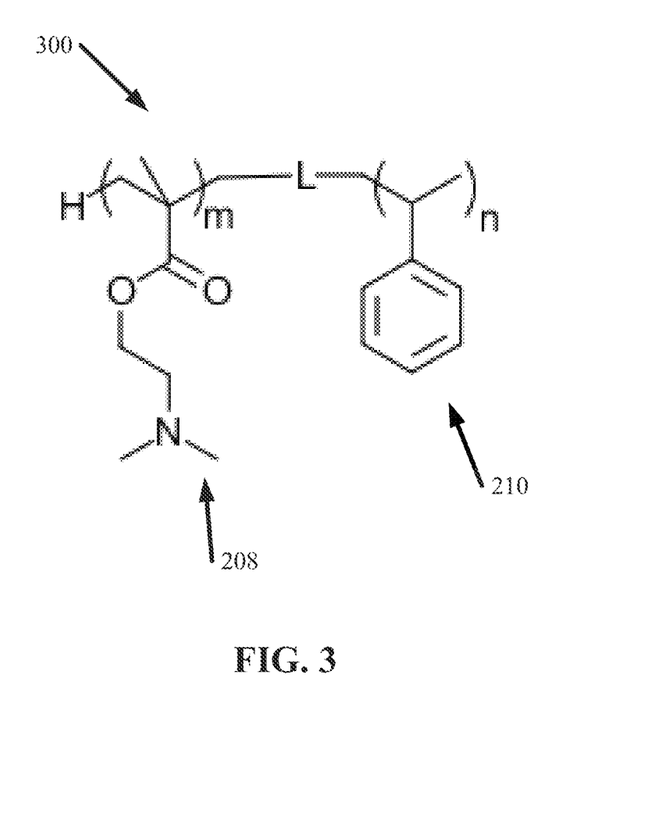
FIG. 3 illustrates a diagram of an example, non-limiting chemical structure that can characterize the structure of one or more arms that can comprise a loaded star polymer in accordance with one or more embodiments described herein.

FIG. 3 illustrates a drawing of an example, non-limiting chemical structure 300 for an arm 102 of the plurality of arms 102. Repetitive description of like elements employed in other embodiments described herein is omitted for sake of brevity. In one or more embodiments, the arms 102 of the loaded star polymer 100 can have a structure characterized by chemical structure 300. In various embodiments, one or more of the arms 102 comprising the loaded star polymer 100 can have a structure characterized by a chemical structure different than chemical structure 300 in accordance with the embodiments described herein. Also, in one or more embodiments, substantially all, or all, of the arms 102 can have a structure characterized by a chemical structure different than chemical structure 300 in accordance with the embodiments described herein.

In some embodiments, the "H" illustrated in chemical structure 300 can represent the reactive end group 206. In one or more embodiments, one or more of the arms 102 can have a structure characterized by chemical structure 300 without "H." Additionally, the "L" illustrated in chemical structure 300 can indicate a linkage group. Example linkage groups can include, but are not limited to: an ester, an amide, a thioester, a hydrocarbon group with a number of carbon atoms greater than or equal to 2 and less than or equal to 10, a combination thereof, and the like. Wherein the arms 102 have a structure characterized by chemical structure 300, the second unit 210 can be polystyrene and the respective second blocks 204 of the arms 102 can crosslink to form a polystyrene polymer core 104.

Referring again to FIG. 1, one or more singlet oxygen generators 106 can be loaded within and/or adjacent to the polymer core 104. The one or more singlet oxygen generators 106 can comprise greater than or equal to one percent by weight of the loaded star polymer 100 and less than or equal to fifty percent by weight of the loaded star polymer 100. Also, the one or more singlet oxygen generators 106 can generate singlet oxygen species in response to light. The light can be visible or ultra-violet ("UV") light having a wavelength greater than or equal to 10 nanometers and less than or equal to 750 nanometers. The one or more singlet oxygen generators 106 can be encapsulated within the loaded star polymer 100, wherein the one or more singlet oxygen generators 106 can be bound to the arms 102 via non-covalent interactions. Further, the one or more singlet oxygen generators 106 can be presented in the loaded star polymer 100 in molecular form, or as a nanoparticle having an average size greater than or equal to 1 nanometer and less than or equal to 10 nanometers.

One or more singlet oxygen generators 106 can be derived from a molecule selected from a group comprising, but not limited to: a porphyrin, a phthalocyanine, a phenothiazine, xanthene, quinone, a combination thereof, and/or the like. For example, in various embodiments the singlet oxygen generator 106 can comprise a metal porphyrinoid compound. In some embodiments, all the singlet oxygen generators 106 encapsulated within the loaded star polymer 100 can have the same chemical structure (e.g., a porphyrin derivative structure). In one or more embodiments, one or more singlet oxygen generators 106 encapsulated within a subject loaded star polymer 100 can have a first chemical structure (e.g., a porphyrin derivative structure) while one or more other singlet oxygen generators 106 encapsulated within the subject loaded star polymer 100 can have another chemical structure (e.g., a phthalocyanine derivative structure, a phenothiazine derivative structure, a xanthene derivative structure, a quinone derivative structure, and/or a combination thereof). Additionally, in various embodiments, the one or more singlet oxygen generators 106 can be non-degradable. In other embodiments, any other compounds that exhibit ROS generation can comprise the singlet oxygen generator 106.

Figure 4:
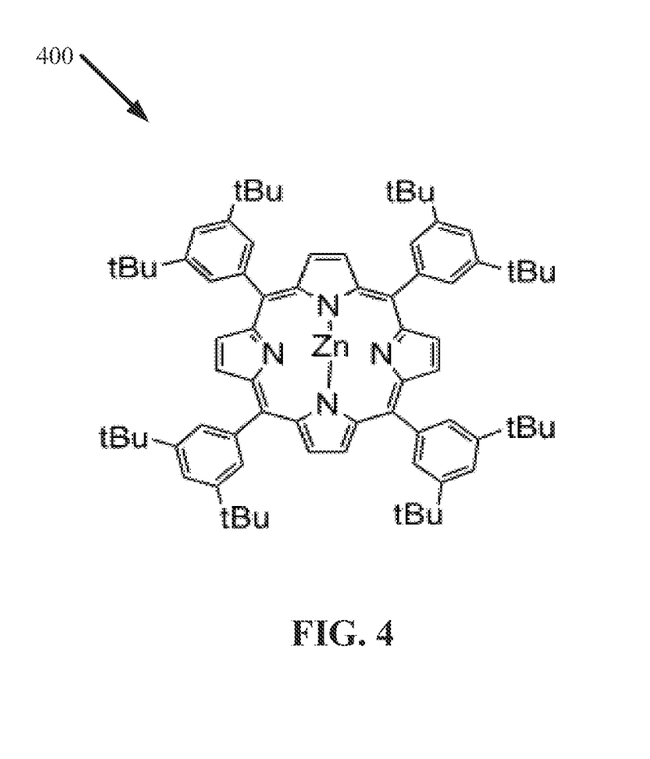
FIG. 4 illustrates a diagram of an example, non-limiting chemical structure that can characterize the structure of one or more singlet oxygen generators that can comprise a loaded star polymer in accordance with one or more embodiments described herein.

FIG. 4 illustrates a drawing of an example, non-limiting chemical structure 400 of a singlet oxygen generator 106. Repetitive description of like elements employed in other embodiments described herein is omitted for sake of brevity. As shown in FIG. 4, an example singlet oxygen generator 106 can be [5,10,15,20-tetra(3,5-ditertbutylphenyl)porphyrinato]Zinc(II). In one or more embodiments, the one or more singlet oxygen generators 106 can have a structure characterized by chemical structure 400. In various embodiments, one or more of the singlet oxygen generators 106 can have a structure characterized by a chemical structure different than chemical structure 400 in accordance with the embodiments described herein. For example, in various embodiments the loaded star polymer 100 can comprise: a singlet oxygen generator 106 derived from porphyrin and having a structure characterized by chemical structure 400; and another singlet oxygen generator 106 derived from a phthalocyanine, a phenothiazine, xanthene, and/or quinone, thereby having a structure not characterized by chemical structure 400. Also, in one or more embodiments, substantially all, or all, of the singlet oxygen generators 106 can have a structure characterized by a chemical structure different than chemical structure 400.

Thus, in various embodiments a polymer (e.g., loaded star polymer 100) can comprise a plurality (e.g., greater than or equal to six and less than or equal to one hundred) of non-degradable copolymer arms 102 that can have respective first ends (e.g., second block 204) and respective second ends (e.g., first block 202). The respective first ends (e.g., second block 204) can be crosslinked to form a vinyl polymer core 104 (e.g., via the second unit 210). For example, the second unit 210 can be one or more groups of polystyrene, wherein crosslinking of the second units 210 of a plurality of arms 102 can form a polystyrene polymer core 104. The respective second ends (e.g., first block 202) can have antimicrobial functionality (e.g., via first unit 208). For example, the second ends (e.g., first block 202) can be positively charged (e.g., via first unit 208) to facilitate electrostatic disruption of a microbial membrane. One or more of the non-degradable copolymer arms 102 can have a structure characterized by chemical structure 300. Also, the polymer (e.g., loaded star polymer 100) can further comprise a singlet oxygen generator 106 loaded within the vinyl polymer core 104, wherein the singlet oxygen generator 106 can generate a singlet oxygen species in response to light (e.g., light having a wavelength greater than or equal to 10 nanometers and less than or equal to 750 nanometers). Additionally, the singlet oxygen generator 106 can be derived from a molecule selected from a group consisting of porphyrin, a phthalocyanine, a phenothiazine, xanthene, and/or quinone. For example, the singlet oxygen generator 106 can be derived from porphyrin. Further, a porphyrin derived singlet oxygen generator 106 can have a structure characterized by chemical structure 400. Furthermore, the singlet oxygen generator 106 can comprise greater than or equal to one percent by weight of the polymer (e.g., loaded star polymer 100) and less than or equal to fifty percent by weight of the polymer (e.g., loaded star polymer 100).

Figure 5:
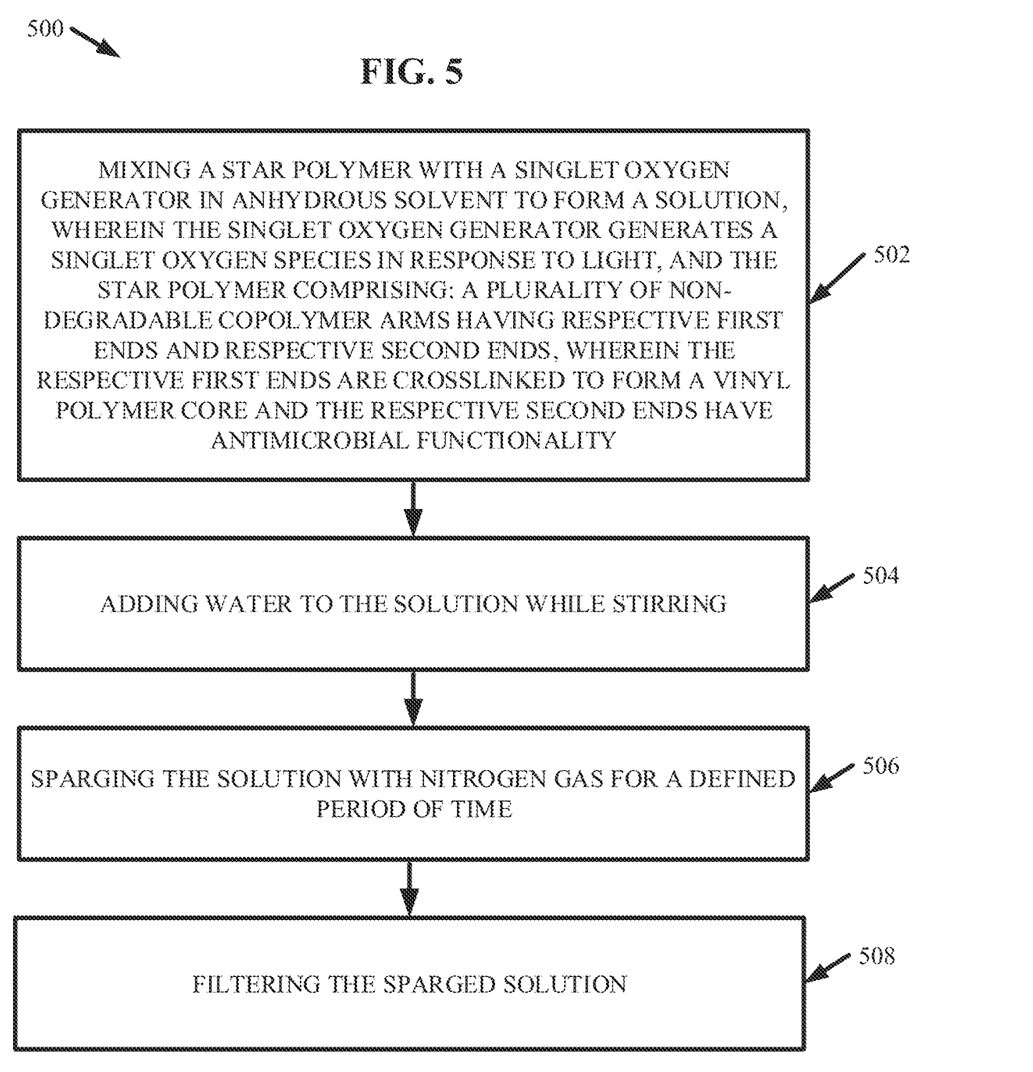
FIG. 5 illustrates a flow diagram of an example, non-limiting method that can facilitate production of a star polymer loaded with one or more singlet oxygen generators in accordance with one or more embodiments described herein.

FIG. 5 illustrates a flow diagram of an example, non-limiting method 500 for preparing the loaded star polymer 100. Repetitive description of like elements employed in other embodiments described herein is omitted for sake of brevity. In various embodiments, one or more star polymers comprising the plurality of arms 102 and the polymer core 104 can be prepared using polymerization methods known in the art. Also, one or more singlet oxygen generators 106 can be prepared using polymerization methods known in the art.

At 502, the method 500 can comprise mixing the one or more prepared star polymers comprising the plurality of arms 102 and the polymer core 104 with the one or more prepared singlet oxygen generators 106. In various embodiments, the one or more star polymers and the one or more singlet oxygen generators 106 can be mixed in an anhydrous solvent to form a substantially homogeneous solution. Example anhydrous solvents can include, but are not limited to: tetrahydrofuran, acetone, dimethylforamide, dimethylsulfoxide, dioxane, isopropanol, a combination thereof, and/or the like. In some embodiments, the amount of singlet oxygen generators 106 mixed with the star polymer can be greater than or equal to 1 percent by weight of the initial star polymer and less than or equal to 50 percent by weight of the initial star polymer. The mixing can encapsulate the singlet oxygen generator 106 within the loaded star polymer 100. At 504, the method 500 can comprise adding water to the star polymer and singlet oxygen generator 106 solution while stirring. At 506, the solution can be sparged with nitrogen gas for a defined period of time greater than or equal to 30 minutes and less than or equal to 6 hours. At 508, the method 500 can comprise filtering (e.g., via a Nylon filter) the sparged solution. In some embodiments, the filter used in the filtering can have a fineness of greater than or equal to 0.25 microns (μm) and less than or equal to 1 μm.

For example, 20 milligrams of prepared star polymers respectively comprising the plurality of arms 102 and the polymer core 104 (e.g., in accordance with chemical structure 300) can be mixed with 6 milligrams of singlet oxygen generators 106 (e.g., in accordance with chemical structure 400) in 0.2 milliliters of tetrahydrofuran to form a homogeneous solution. Additionally, 4 milliliters of water can be rapidly added to the homogeneous solution while stirring. The resulting solution can be sparged with nitrogen gas for approximately three hours to remove organic solvent residue and can be filtered through a 0.4 μm Nylon filter.

Thus, in one or more embodiments the method 500 can comprise mixing (e.g., at 502) a star polymer with a singlet oxygen generator 106 in an anhydrous solvent (e.g., tetrahydrofuran, acetone, dimethylforamide, dimethylsulfoxide, dioxane, and/or isopropanol) to form a solution. The singlet oxygen generator 106 can generate a singlet oxygen species in response to light (e.g., light having a wavelength greater than or equal to 10 nanometers and less than or equal to 750 nanometers). The mixing can encapsulate the singlet oxygen generator 106 within the star polymer. Further the star polymer can comprise a plurality (e.g., greater than or equal to six and less than or equal to one hundred) of non-degradable copolymer arms 102 that can have respective first ends (e.g., second block 204) and respective second ends (e.g., first block 202). The respective first ends (e.g., second block 204) can be crosslinked to form a vinyl polymer core 104 (e.g., via the second unit 210). For example, the second unit 210 can be one or more groups of polystyrene, wherein crosslinking of the second units 210 of a plurality of arms 102 can form a polystyrene polymer core 104. The respective second ends (e.g., first block 202) can have antimicrobial functionality (e.g., via first unit 208). For example, the second ends (e.g., first block 202) can be positively charged (e.g., via first unit 208) to facilitate electrostatic disruption of a microbial membrane. One or more of the non-degradable copolymer arms 102 can have a structure characterized by chemical structure 300. Additionally, the singlet oxygen generator 106 can be derived from a molecule selected from a group consisting of porphyrin, a phthalocyanine, a phenothiazine, xanthene, and/or quinone. For example, the singlet oxygen generator 106 can be derived from porphyrin. Further, a porphyrin derived singlet oxygen generator 106 can have a structure characterized by chemical structure 400. Also, the method 500 can comprise adding water to the solution while stirring (e.g., at 504) prior to sparging the solution with nitrogen gas (e.g., at 506) for a defined period of time (e.g., greater than or equal to 30 minutes and less than or equal to 6 hours), and filtering the sparged solution (e.g., at 508) through a filter (e.g., a Nylon filter having a fineness greater than or equal to 0.25 μm and less than or equal to 1 μm).

The loaded star polymer 100 described herein can exhibit at least two mechanisms to facilitate antimicrobial functionality. Regarding the first mechanism, the plurality of arms

102 (e.g., via the first block 202 and/or the first unit 208) can electrostatically disrupt a membrane of a pathogen (e.g., a Gram-negative bacteria, a Gram-positive bacteria, fungi, yeast, a combination thereof, and/or the like). Regarding the second mechanism, the one or more singlet oxygen generators 106 can generate one or more singlet oxygen species in response to the loaded star polymer 100 being irradiated by light, wherein the singlet oxygen species can facilitate degradation of the pathogen. In various embodiments, the loaded star polymer 100 can exhibit higher antimicrobial efficacy than conventional star polymers (e.g., due at least in part to the one or more singlet oxygen generators 106) while maintaining greater stability than conventional singlet oxygen generators.

Figure 6:
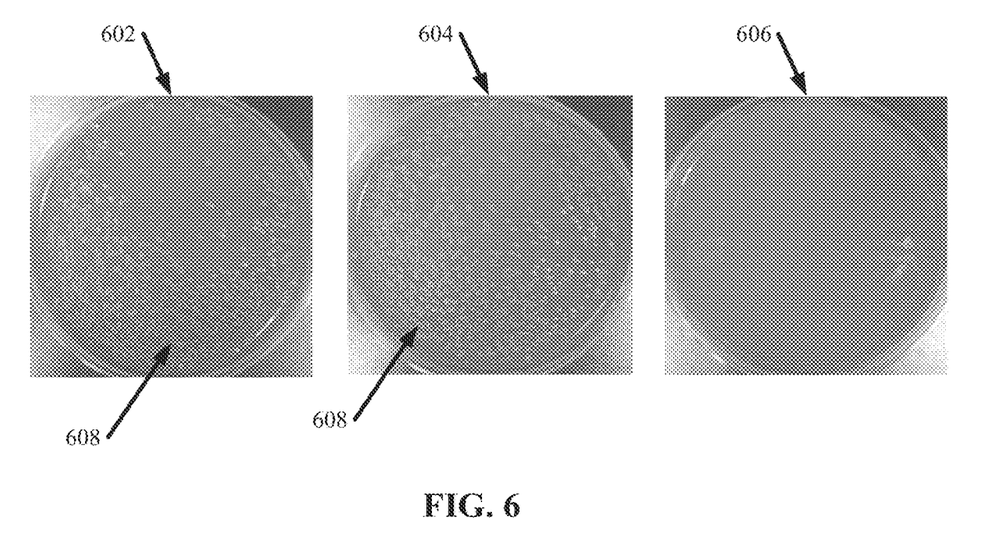
FIG. 6 illustrates three photos of example, non-limiting agar plates to demonstrate the antimicrobial efficacy of a star polymer loaded with one or more singlet oxygen generators in accordance with one or more embodiments described herein.

FIG. 6 illustrates three photos of example, non-limiting blood agar plates used to demonstrate the unexpected antimicrobial efficacy of the loaded star polymer 100. Repetitive description of like elements employed in other embodiments described herein is omitted for sake of brevity. A first agar plate 602 can comprise only a growth solution (e.g., sodium chloride) and bacterial culture. A second agar plate 604 can comprise a growth solution (e.g., sodium chloride), bacterial culture, and a star polymer comprising the plurality of arms 102 and the polymer core 104 described herein. A third agar plate 606 can comprise a growth solution (e.g., sodium chloride), bacterial culture, and the loaded star polymer 100 in accordance with the various embodiments described herein.

FIG. 6 shows the first agar plate 602, the second agar plate 604, and the third agar plate 606 after the plates have been exposed to sunlight for two hours. As shown in FIG. 6, numerous bacterial colonies 608 formed within the first agar plate 602 and the second agar plate 604. However, little to no bacterial colonies 608 formed within the third agar plate 606. Thus, FIG. 6 demonstrates the antimicrobial efficacy of the loaded star polymer 100.

In order to confirm that antimicrobial activity of the loaded star polymer 100 was a result of, at least in part, ROS generation, rather than from a slow release of a potentially toxic derivative of the singlet oxygen generator 106; release of the singlet oxygen generator was monitored over a twenty-four hour time period. The loaded star polymer 100 utilized in the third agar plate 606 was immersed in deuterium oxide ("heavy water"), then aliquots were collected after two hours, four hours, six hours, and twelve hours. The aliquots were analyzed using proton nuclear magnetic resonance ("¹H NMR") technology. No measurable amount of the singlet oxygen generator 106 was detected in any of the aliquots.

In order to confirm the generation of ROS by the encapsulated singlet oxygen generator 106, a water-soluble dye (e.g., 9,10-anthracene dipropionic acid diosodium salt "ADPA") was introduced to the loaded star polymer 100. ADPA reacts with singlet oxygen according to scheme 1 below:

Scheme 1

Singlet oxygen induced bleaching of the ADPA dye in the presence of the loaded star polymer 100 was monitored by UV-vis spectroscopy. A solution of the water-soluble dye, water, and the loaded star polymer 100 was exposed to sunlight for thirty minutes. An aliquot of the solution was taken every five minutes and analyzed.

Figure 7:
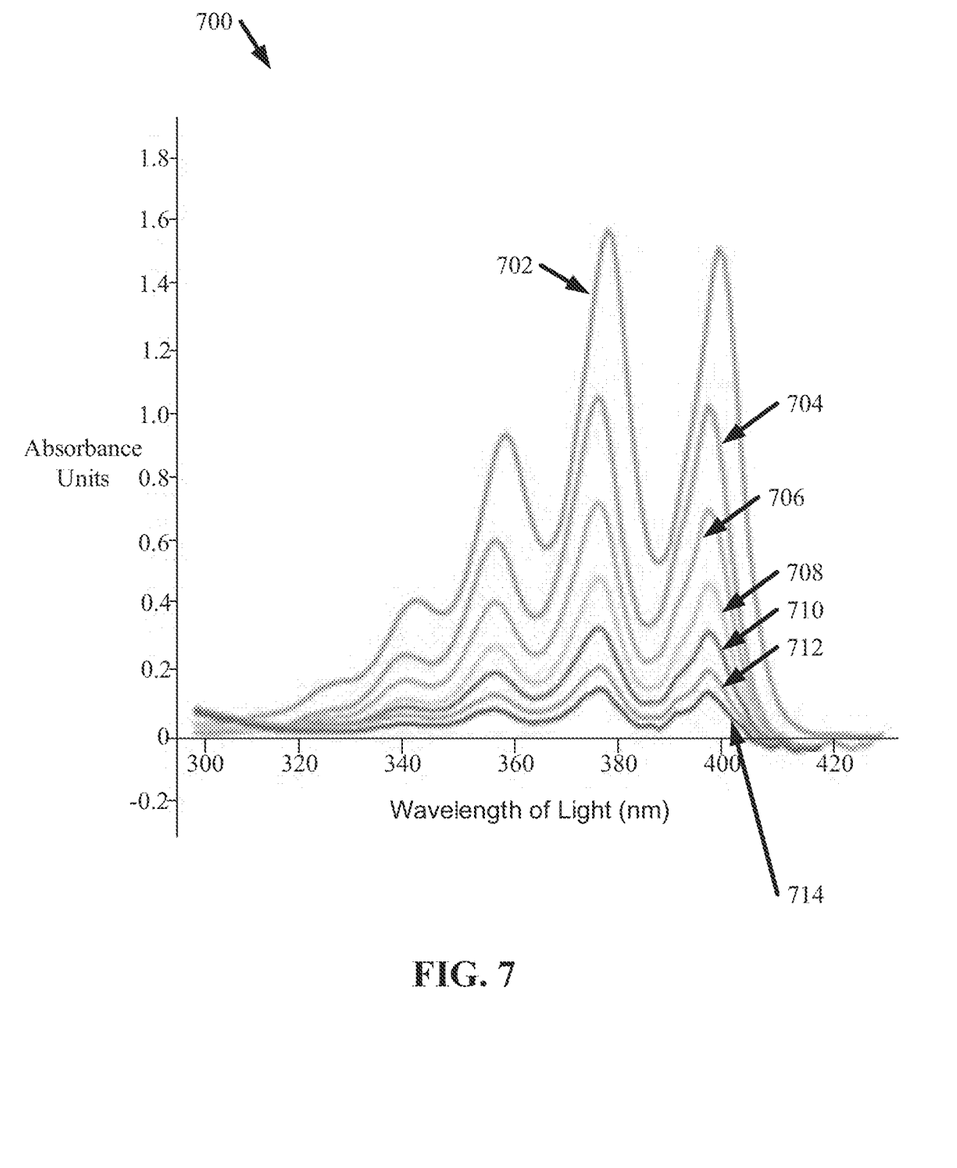
FIG. 7 illustrates a diagram of an example, non-limiting graph to demonstrate the antimicrobial efficacy of a star polymer loaded with one or more singlet oxygen generators in accordance with one or more embodiments described herein.
Figure 8:
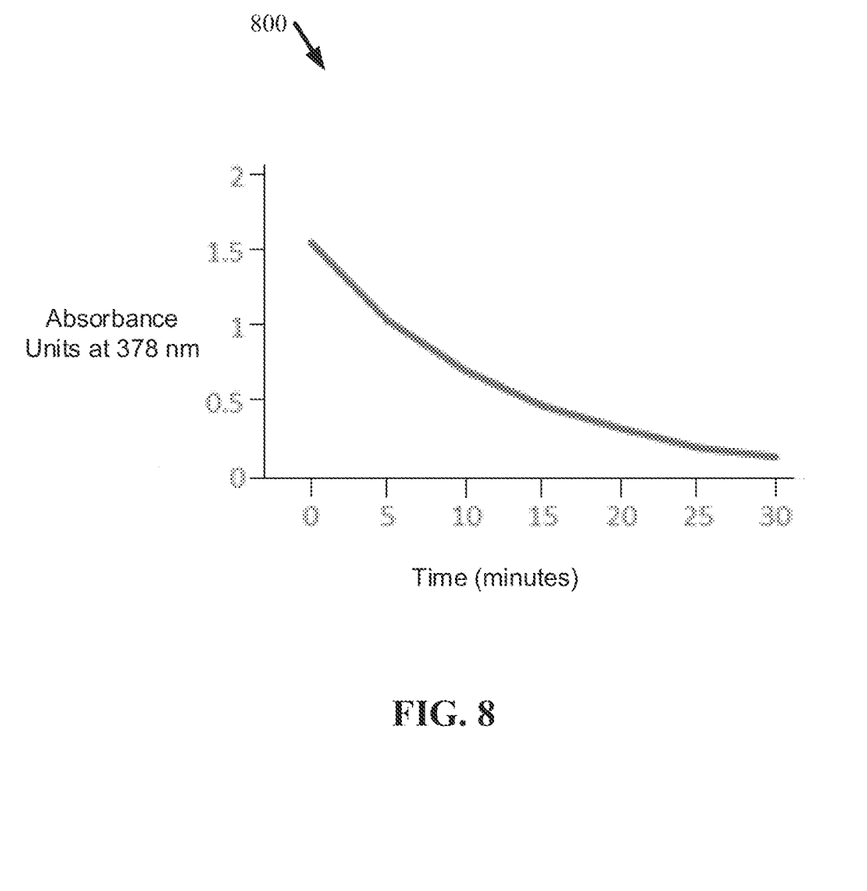
FIG. 8 illustrates a diagram of another example, non-limiting graph to demonstrate the antimicrobial efficacy of a star polymer loaded with one or more singlet oxygen generators in accordance with one or more embodiments described herein.

FIG. 7 illustrates a graph 700 showing the absorption spectrum of the ADPA dye. Repetitive description of like elements employed in other embodiments described herein is omitted for sake of brevity. The first line 702 represents the aliquot of ADPA at zero minutes. The second line 704 represents the aliquot of ADPA taken at five minutes. The third line 706 represents the aliquot of ADPA taken at ten minutes. The fourth line 708 represents the aliquot of ADPA taken at fifteen minutes. The fifth line 710 represents the aliquot of ADPA taken at twenty minutes. The sixth line 712 represents the aliquot of ADPA taken at twenty-five minutes. The seventh line 714 represents the aliquot of ADPA taken at thirty minutes. Graph 700 illustrates a decrease in the ADPA's absorption as time progressed. FIG. 8 illustrates another graph 800 that further shows the rapid decrease in the absorbance peak of the ADPA. Repetitive description of like elements employed in other embodiments described herein is omitted for sake of brevity. The rapid decrease is attributed to the reaction with singlet oxygen generated by the singlet oxygen generator 106 encapsulated in the loaded star polymer 100.

The results illustrated in graph 700 and graph 800 confirm that encapsulation of a singlet oxygen generator 106 in a polymer matrix (e.g., loaded star polymer 100) does not interfere with the singlet oxygen generator's 106 ability to generate a singlet oxygen species. Further, in order to verify that there was no release of photosensitizer in the media, the loaded star polymers 100 were kept under irradiation in heavy water for three hours, aliquots were collected and analyzed by ¹H NMR technology, and no measurable amount of singlet oxygen generator was detected in the heavy water.

In various embodiments, the loaded star polymer 100 described herein can be used to create a film-forming composition to facilitate surface treatment of various articles such as, but not limited to, food packages and/or medical devices. The film-forming composition can comprise a solvent and one or more of the loaded star polymers 100 described herein, wherein the one or more loaded star polymers 100 can be dispersed in the solvent. In various embodiments, the loaded star polymer 100 can comprise greater than or equal to 0.1 weight percent of the film-forming composition and less than or equal to 50 weight percent of the film-forming composition. In some embodiments, the loaded star polymer 100 can comprise greater than or equal to 5 weight percent of the film-forming composition and less than or equal to 20 weight percent of the film-forming composition.

Thus, in one or more embodiments a film-forming composition can comprise a solvent (e.g., water and/or an organic solvent) and a star polymer (e.g., loaded star polymer 100). The star polymer (e.g., loaded star polymer 100) can comprise greater than or equal to 5 weight percent of the film-forming composition and less than or equal to 20 weight percent of the film-forming composition. The star polymer (e.g., loaded star polymer 100) can be dispersed in the solvent. Also, the star polymer (e.g., loaded star polymer 100) can comprise can comprise a plurality (e.g., greater than or equal to six and less than or equal to one hundred) of non-degradable copolymer arms 102 that can have respective first ends (e.g., second block 204) and respective second ends (e.g., first block 202). The respective first ends (e.g., second block 204) can be crosslinked to form a vinyl polymer core 104 (e.g., via the second unit 210). For example, the second unit 210 can be one or more groups of polystyrene, wherein crosslinking of the second units 210 of a plurality of arms 102 can form a polystyrene polymer core 104. The respective second ends (e.g., first block 202) can have antimicrobial functionality (e.g., via first unit 208). For example, the second ends (e.g., first block 202) can be positively charged (e.g., via first unit 208) to facilitate electrostatic disruption of a microbial membrane. One or more of the non-degradable copolymer arms 102 can have a structure characterized by chemical structure 300. Also, the star polymer (e.g., loaded star polymer 100) can further comprise a singlet oxygen generator 106 loaded within the vinyl polymer core 104, wherein the singlet oxygen generator 106 can generate a singlet oxygen species in response to light (e.g., light having a wavelength greater than or equal to 10 nanometers and less than or equal to 750 nanometers). Additionally, the singlet oxygen generator 106 can be derived from a molecule selected from a group consisting of porphyrin, a phthalocyanine, a phenothiazine, xanthene, and/or quinone. For example, the singlet oxygen generator 106 can be derived from porphyrin. Further, a porphyrin derived singlet oxygen generator 106 can have a structure characterized by chemical structure 400. Furthermore, the singlet oxygen generator 106 can comprise greater than or equal to one percent by weight of the star polymer (e.g., loaded star polymer 100) and less than or equal to fifty percent by weight of the star polymer (e.g., loaded star polymer 100). The film-forming composition can be toxic to a pathogen (e.g., a Gram-negative bacteria, a Gram-positive bacteria, fungi, and/or yeast).

In one or more embodiments, the film-forming composition can additionally comprise one or more additives to increase efficacy. Example additives can include, but are not limited to: an antimicrobial metal (e.g., nanoparticles of silver, gold, and/or copper), ceramic nanoparticles (e.g., titanium dioxide and/or zinc oxide), antimicrobial metal salts, a pigment, a surfactant, a thickener, an accelerator to speed crosslinking between loaded star polymers 100, a combination thereof, and/or the like.

In various embodiments, the loaded star polymers 100 do not readily crosslink with other star polymers (e.g., other loaded star polymers 100) in the presence of the solvent; rather, said crosslinking is performed upon removal of the solvent. Thus, the film-forming composition can exhibit a stable shelf life. Example solvents include, but are not limited to: water, an organic solvent, a combination thereof, and/or the like.

Figure 9:
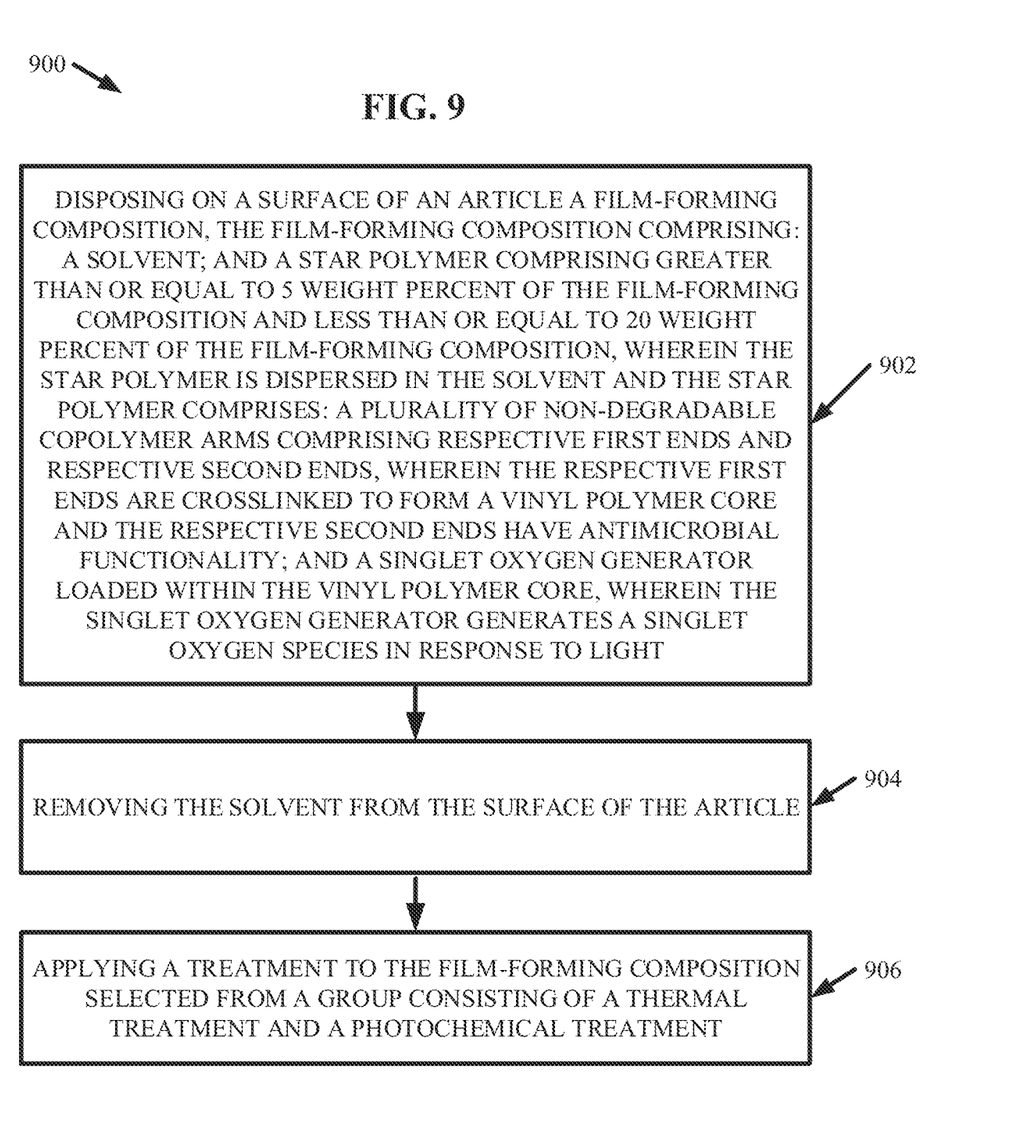
FIG. 9 illustrates a flow diagram of an example, non-limiting method that can facilitate surface treating an article with a star polymer loaded with one or more singlet oxygen generators in accordance with one or more embodiments described herein.

FIG. 9 illustrates a flow diagram of an example, non-limiting method 900 for forming a surface treated article. Repetitive description of like elements employed in other embodiments described herein is omitted for sake of brevity. Example articles that can be treated via method 900 include, but are not limited to: food packaging, medical devices, floor surfaces, furniture surfaces, wound care instruments (e.g., bandages and/or gauss), building surfaces, plants (e.g., agricultural crops), ground surfaces, farming equipment, beds, sheets, clothes, blankets, shoes, doors, door frames, walls, ceilings, mattresses, light fixtures, facets, switches, sinks, grab rails, remote controls, vanities, computer equipment, carts, trolleys, hampers, bins, a combination thereof, and/or the like.

At 902, the method 900 can comprise disposing on a surface of an article the film-forming composition described herein. For example, the film-forming composition can comprise the loaded star polymer 100 dispersed within a solvent. The film-forming composition can be disposed on the surface via a variety of techniques including, but not limited to: dipping, spraying, spin coating, brushing, a combination thereof, and/or the like. In various embodiments, disposing the film-forming composition coats the surface of the article with an initial layer of loaded star polymers 100 that are not crosslinked to other star polymers (e.g., other loaded star polymers 100). At 904, the method 900 can comprise removing the solvent from the film-forming composition, and thereby, the surface of the coated article. The solvent can be removed via evaporation (e.g., by ambient conditions and/or a drying treatment, such as heated air). Upon removing the solvent, the loaded star polymers 100 left residing on the surface of the article can begin to crosslink with each other, thereby forming a crosslinked film layer on the surface of the article.

At 906, the method can optionally include a thermal and/or photochemical treatment of the surface to facilitate crosslinking between loaded star polymers 100. For example, subsequent to removal of the solvent, the resulting film layer can be cured by heating the film layer to a temperature greater than the first block 202 and/or the second block 204.

The thickness of the crosslinked film layer of loaded star polymers 100 on the surface of the treated article can vary depending on the concentration of the film-forming composition and/or the dispersing technique. In one or more embodiments, the method 900 can form a crosslinked layer having a thickness substantially equivalent to one loaded star polymer 100. In some embodiments, the method 900 can form a crosslinked layer having a thickness substantially equivalent to a plurality of loaded star polymers 100. Additionally, the crosslinked film layer can exhibit an opacity greater than or equal to 0% and less than or equal to 100%, with any suitable light absorbing and/or light transmission properties. Further, the crosslinked film layer can be any hue, including, but not limited to, red, yellow, blue or combinations thereof.

In various embodiments, the crosslinked film formed by the method 900 can adhere to a variety of surface materials including, but not limited to: metal surfaces, glass surfaces, plastic surfaces, ceramic surfaces, wood surfaces, stone surfaces, textile surfaces, paper surfaces, cloth surfaces, concrete surfaces, synthetic fiber surfaces, organic fiber surfaces, a combination thereof, and/or the like. Furthermore, in one or more embodiments the crosslinked film layer can be treated with one or more chemical agents (e.g., alkylating agents) to increase the antimicrobial effect of the crosslinked film layer. In some embodiments, biocompatible forms of the loaded star polymer 100 can be utilized with method 900 to form biocompatible crosslinked films that can surface treat insertable medical devices.

In one or more embodiments, the treated surface comprising the crosslinked film layer can be irradiated with light to facilitate on-demand enhanced antimicrobial functionality. For example, the one or more singlet oxygen generators 106 encapsulated within the one or more loaded star polymers 100 that comprise the crosslinked film layer can generate one or more singlet oxygen species in response to the light. Subsequent to being irradiated with light, the crosslinked film layer can be recovered from the article's surface so as to recycle the plurality of arms 102 and polymer core 104. Recycling can comprise using the recovered plurality of arms 102 and polymer core 104 as a prepared star polymer in accordance with method 500 to generate one or more new loaded star polymers 100.

Thus, in various embodiments a method 900 of forming a surface treated article can comprise disposing (e.g., at 902) on a surface of an article a film-forming composition. The film-forming composition can comprise a solvent (e.g., water and/or an organic solvent) and a star polymer (e.g., loaded star polymer 100). The star polymer (e.g., loaded star polymer 100) can comprise greater than or equal to 5 weight percent of the film-forming composition and less than or equal to 20 weight percent of the film-forming composition. The star polymer (e.g., loaded star polymer 100) can be dispersed in the solvent. Also, the star polymer (e.g., loaded star polymer 100) can comprise can comprise a plurality (e.g., greater than or equal to six and less than or equal to one hundred) of non-degradable copolymer arms 102 that can have respective first ends (e.g., second block 204) and respective second ends (e.g., first block 202). The respective first ends (e.g., second block 204) can be crosslinked to form a vinyl polymer core 104 (e.g., via the second unit 210). For example, the second unit 210 can be one or more groups of polystyrene, wherein crosslinking of the second units 210 of a plurality of arms 102 can form a polystyrene polymer core 104. The respective second ends (e.g., first block 202) can have antimicrobial functionality (e.g., via first unit 208). For example, the second ends (e.g., first block 202) can be positively charged (e.g., via first unit 208) to facilitate electrostatic disruption of a microbial membrane. One or more of the non-degradable copolymer arms 102 can have a structure characterized by chemical structure 300. Also, the star polymer (e.g., loaded star polymer 100) can further comprise a singlet oxygen generator 106 loaded within the vinyl polymer core 104, wherein the singlet oxygen generator 106 can generate a singlet oxygen species in response to light (e.g., light having a wavelength greater than or equal to 10 nanometers and less than or equal to 750 nanometers). Additionally, the singlet oxygen generator 106 can be derived from a molecule selected from a group consisting of porphyrin, a phthalocyanine, a phenothiazine, xanthene, and/or quinone. For example, the singlet oxygen generator 106 can be derived from porphyrin. Further, a porphyrin derived singlet oxygen generator 106 can have a structure characterized by chemical structure 400. Furthermore, the singlet oxygen generator 106 can comprise greater than or equal to one percent by weight of the star polymer (e.g., loaded star polymer 100) and less than or equal to fifty percent by weight of the star polymer (e.g., loaded star polymer 100). The film-forming composition can be toxic to a pathogen (e.g., a Gram-negative bacteria, a Gram-positive bacteria, fungi, and/or yeast). Also, the method 900 can comprise removing the solvent (e.g., at 904) from the surface of the article, and optionally applying a treatment (e.g., at 906) to the film-forming composition (e.g., a thermal treatment and/or a photochemical treatment).

Figure 10:
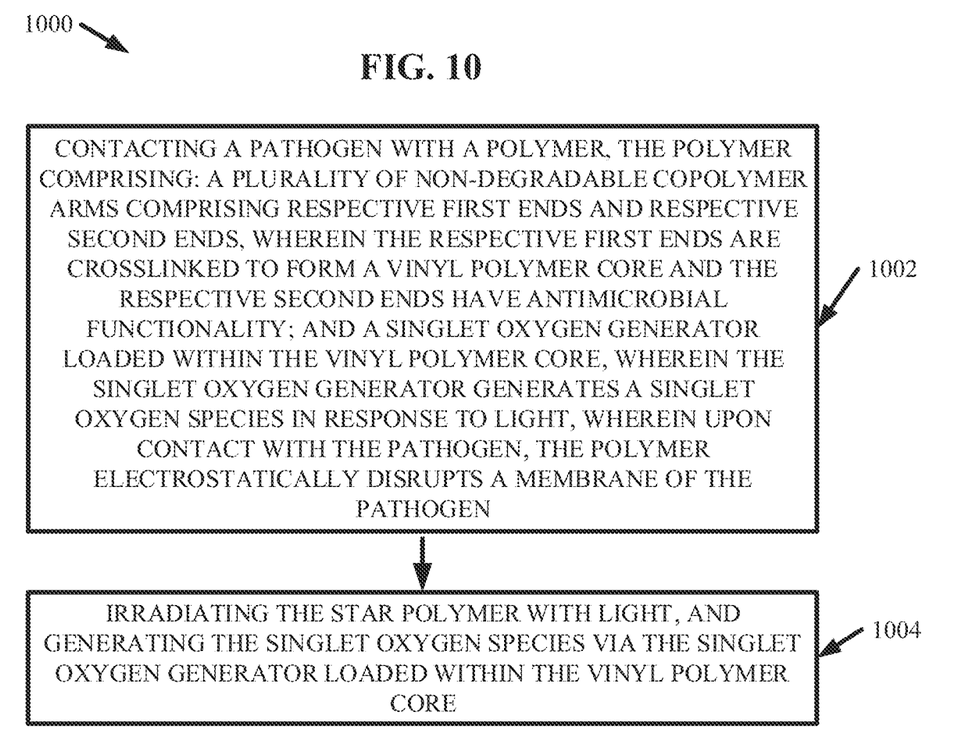
FIG. 10 illustrates a flow diagram of an example, non-limiting method that can facilitate killing a pathogen with a star polymer loaded with one or more singlet oxygen generators in accordance with one or more embodiments described herein.

FIG. 10 illustrates another flow diagram of an example, non-limiting method 1000 of killing a pathogen, preventing the growth of a pathogen, and/or preventing contamination by a pathogen. Repetitive description of like elements employed in other embodiments described herein is omitted for sake of brevity. Example pathogens include, but are not limited to: Gram-negative bacteria, Gram-positive bacteria, fungi, yeast, a combination thereof, and/or the like.

At 1002, the method 1000 can comprise contacting one or more of the loaded star polymers 100 (e.g., via a crosslinked film formed on the surface of an article in accordance to method 900) with a pathogen. In various embodiments, upon contact, the plurality of arms 102 can electrostatically disrupt a membrane of the pathogen. In one or more embodiments, the one or more loaded star polymers 100 can be located on the surface of an article, whereupon the contacting can comprise a physical meeting of the article's treated surface with the pathogen. In some embodiments, the pathogen can be located on the surface of an article, whereupon the contacting can comprise a physical meeting of the one or more loaded star polymers 100 with the pathogen. For example, the pathogen can be located on an article and the contacting at 1002 can comprise coating the contaminated article with the film-forming composition described herein. For instance, the pathogen can be located on a crop, wherein the contaminated crop can be sprayed with a film-forming composition comprising the loaded star polymer 100.

At 1004, the method 1000 can further comprise irradiating one or more of the loaded star polymers 100 in contact with the pathogen with light. For example, the light can have a wavelength greater than or equal to 10 nanometers and less than or equal to 750 nanometers. In various embodiments, the one or more loaded star polymers 100 irradiated with light can respond by generating a singlet oxygen species (e.g., via the singlet oxygen generator 106 encapsulated within the loaded star polymer 100), wherein the singlet oxygen species can facilitate degradation of the pathogen. Thus, the antimicrobial effects of method 1000, and thereby the loaded star polymer 100, can be increased on demand via controlled irradiation of the one or more loaded star polymers 100 with light.

Thus, in one or more embodiments a method 1000 of killing a pathogen can comprise contacting (e.g., at 1002) the pathogen with a polymer. The polymer (e.g., loaded star polymer 100) can comprise a plurality (e.g., greater than or equal to six and less than or equal to one hundred) of non-degradable copolymer arms 102 that can have respective first ends (e.g., second block 204) and respective second ends (e.g., first block 202). The respective first ends (e.g., second block 204) can be crosslinked to form a vinyl polymer core 104 (e.g., via the second unit 210). For example, the second unit 210 can be one or more groups of polystyrene, wherein crosslinking of the second units 210 of a plurality of arms 102 can form a polystyrene polymer core 104. The respective second ends (e.g., first block 202) can have antimicrobial functionality (e.g., via first unit 208). For example, the second ends (e.g., first block 202) can be positively charged (e.g., via first unit 208) to facilitate electrostatic disruption of a microbial membrane. One or more of the non-degradable copolymer arms 102 can have a structure characterized by chemical structure 300. Also, the polymer (e.g., loaded star polymer 100) can further comprise a singlet oxygen generator 106 loaded within the vinyl polymer core 104, wherein the singlet oxygen generator 106 can generate a singlet oxygen species in response to light (e.g., light having a wavelength greater than or equal to 10 nanometers and less than or equal to 750 nanometers). Additionally, the singlet oxygen generator 106 can be derived from a molecule selected from a group consisting of porphyrin, a phthalocyanine, a phenothiazine, xanthene, and/or quinone. For example, the singlet oxygen generator 106 can be derived from porphyrin. Further, a porphyrin derived singlet oxygen generator 106 can have a structure characterized by chemical structure 400. Furthermore, the singlet oxygen generator 106 can comprise greater than or equal to one percent by weight of the polymer (e.g., loaded star polymer 100) and less than or equal to fifty percent by weight of the polymer (e.g., loaded star polymer 100). Upon contact with the pathogen, the polymer (e.g., loaded star polymer 100) can electrostatically disrupt a membrane of the pathogen. The method 1000 can further comprise irradiating the polymer with the light (e.g., at 1004), thereby generating the singlet oxygen species via the singlet oxygen generator 106 within the polymer core 104.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

What has been described above include mere examples of systems, compositions, and methods. It is, of course, not possible to describe every conceivable combination of reagents, products, solvents, and/or articles for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim. The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A composition, comprising:
a plurality of non-degradable copolymer arms comprising respective first ends and respective second ends, wherein the respective first ends are crosslinked to form a vinyl polymer core and the respective second ends are positively charged to facilitate antimicrobial functionality, wherein the plurality of non-degradable copolymer arms are block copolymers having a structure characterized by the following formula:

wherein m is a first integer greater than or equal to one and less than or equal to one hundred; n is a second integer greater than or equal to one and less than or equal to one hundred; and wherein L represents a linkage group selected from a group consisting of an ester, an amide, a thioester and a hydrocarbon with a number of carbon atoms greater than or equal to 2 and less than or equal to 10; and
a singlet oxygen generator loaded within the vinyl polymer core, wherein the singlet oxygen generator generates a singlet oxygen species in response to light, and wherein the singlet oxygen generator is derived from a molecule from the group consisting of phenothiazine, xanthene, and quinone.

2. The composition of claim 1, wherein the plurality of non-degradable copolymer arms comprises greater than or equal to six non-degradable copolymer arms and less than or equal to one hundred non-degradable copolymer arms.

3. The composition of claim 1, wherein the light has a wavelength greater than or equal to 10 nanometers and less than or equal to 750 nanometers.

4. The composition of claim 1, Wherein the singlet oxygen generator comprises greater than or equal to one percent by weight of the composition and less than or equal to fifty percent by weight of the composition.

* * * * *